US012580066B2

(12) United States Patent
Ming et al.

(10) Patent No.: US 12,580,066 B2
(45) Date of Patent: Mar. 17, 2026

(54) ARTIFICIAL INTELLIGENCE SYSTEM ON AN ELECTRONIC DEVICE

(71) Applicant: Micron Technology, Inc., Boise, ID (US)

(72) Inventors: Kristina L. Ming, Boise, ID (US); Mandy W. Fortunati, Boise, ID (US); Poonam V. Agale, San Jose, CA (US); Ting Zhao, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 965 days.

(21) Appl. No.: 17/649,102

(22) Filed: Jan. 27, 2022

(65) Prior Publication Data

US 2023/0207099 A1    Jun. 29, 2023

Related U.S. Application Data

(60) Provisional application No. 63/266,152, filed on Dec. 29, 2021.

(51) Int. Cl.
*G16H 20/60* (2018.01)
*G06Q 30/0601* (2023.01)
*G16H 20/10* (2018.01)
*G16H 50/20* (2018.01)

(52) U.S. Cl.
CPC ......... *G16H 20/60* (2018.01); *G06Q 30/0633* (2013.01); *G06Q 30/0641* (2013.01); *G16H 20/10* (2018.01); *G16H 50/20* (2018.01)

(58) Field of Classification Search
CPC ........ G16H 20/60; G16H 20/10; G16H 50/20; G06Q 30/0633; G06Q 30/0641; G06Q 30/0631
See application file for complete search history.

(56) References Cited

U.S. PATENT DOCUMENTS

2021/0134434 A1*  5/2021  Riley ..................... G16H 50/30

FOREIGN PATENT DOCUMENTS

WO      WO-2012076755 A1 *  6/2012   ............. G06Q 30/02

OTHER PUBLICATIONS

"NutriStyle Fights Chronic Disease with Healthy Menus." Plus Company Updates Sep. 27, 2018: NA. (Year: 2018).*

* cited by examiner

*Primary Examiner* — Linh Giang Le
(74) *Attorney, Agent, or Firm* — Holland & Hart LLP

(57) ABSTRACT

Methods, systems, and devices for an artificial intelligence system on an electronic device are described. An application on an electronic device may user data from the one or more applications of the electronic device and use the user data to determine criteria for a personalized output for a user. The application may use an artificial intelligence engine to determine the personalized output for the user by applying to the criteria weighting factors that are associated with priority levels for different categories of the criteria. The application may then select items for the user that are in accordance with the personalized output and that are based on the criteria for the personalized output and the priority levels for the different categories of the criteria.

25 Claims, 7 Drawing Sheets

Application Logic

525

Display Logic

535

AI Engine

530

520

500

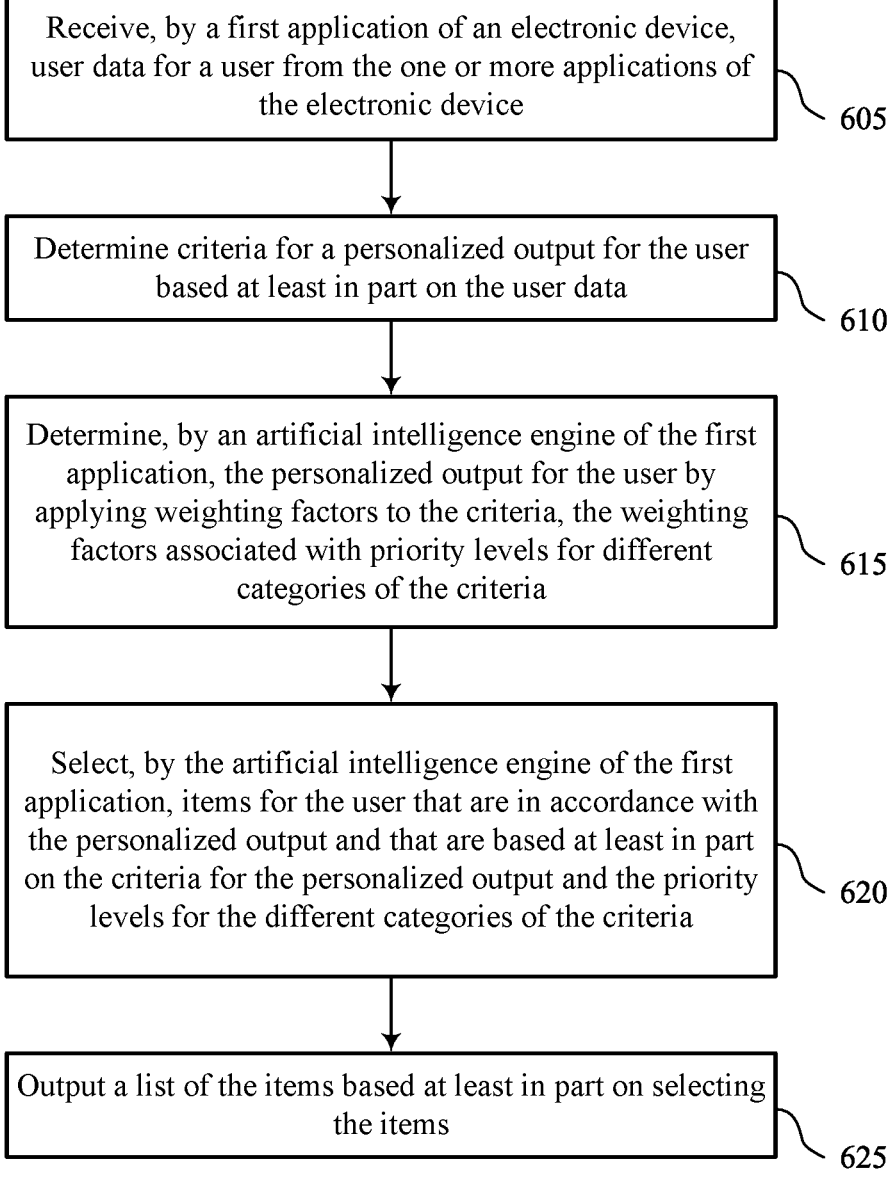

Receive, by a first application of an electronic device, user data for a user from the one or more applications of the electronic device          605

Determine criteria for a personalized output for the user based at least in part on the user data          610

Determine, by an artificial intelligence engine of the first application, the personalized output for the user by applying weighting factors to the criteria, the weighting factors associated with priority levels for different categories of the criteria          615

Select, by the artificial intelligence engine of the first application, items for the user that are in accordance with the personalized output and that are based at least in part on the criteria for the personalized output and the priority levels for the different categories of the criteria          620

Output a list of the items based at least in part on selecting the items          625

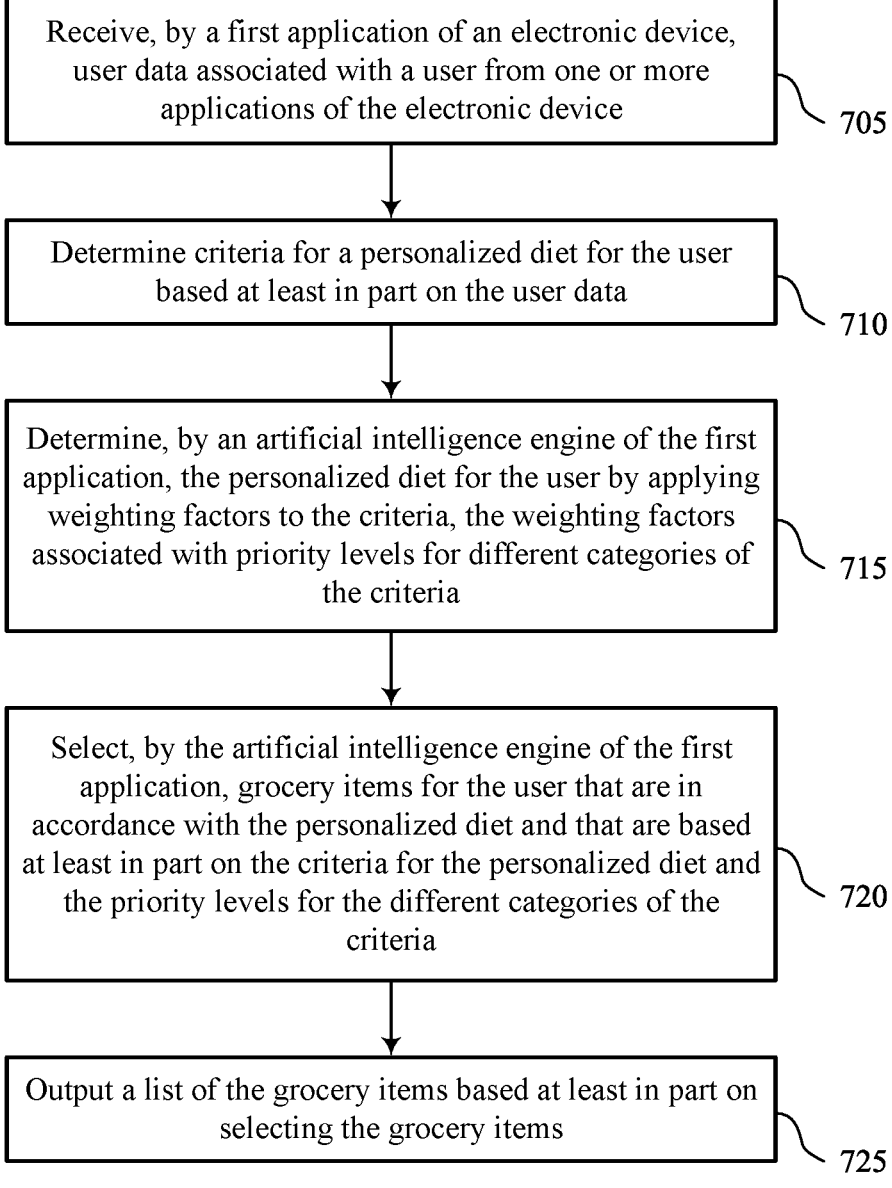

Receive, by a first application of an electronic device, user data associated with a user from one or more applications of the electronic device

705

Determine criteria for a personalized diet for the user based at least in part on the user data

710

Determine, by an artificial intelligence engine of the first application, the personalized diet for the user by applying weighting factors to the criteria, the weighting factors associated with priority levels for different categories of the criteria

715

Select, by the artificial intelligence engine of the first application, grocery items for the user that are in accordance with the personalized diet and that are based at least in part on the criteria for the personalized diet and the priority levels for the different categories of the criteria

720

Output a list of the grocery items based at least in part on selecting the grocery items

ARTIFICIAL INTELLIGENCE SYSTEM ON AN ELECTRONIC DEVICE

CROSS REFERENCE

The present Application for Patent claims the benefit of U.S. Provisional Patent Application No. 63/266,152 by MING et al., entitled "AN ARTIFICIAL INTELLIGENCE SYSTEM ON AN ELECTRONIC DEVICE," filed Dec. 29, 2021, assigned to the assignee hereof, and expressly incorporated by reference herein.

FIELD OF TECHNOLOGY

The following relates generally to an electronic device and more specifically to an artificial intelligence system on an electronic device.

BACKGROUND

Memory devices are widely used to store information in various electronic devices such as computers, user devices, wireless communication devices, cameras, digital displays, and the like. Information is stored by programing memory cells within a memory device to various states. For example, binary memory cells may be programmed to one of two supported states, often denoted by a logic 1 or a logic 0. In some examples, a single memory cell may support more than two states, any one of which may be stored. To access the stored information, a component may read at least one stored state in the memory device. To store information, a component may write the state in the memory device. In some examples, the information stored by a memory device may be associated with an application that is executed by an electronic device that includes the memory device.

BRIEF DESCRIPTION OF THE DRAWINGS

FIGS. 6 and 7 show flowcharts illustrating a method or methods that support an artificial intelligence system on an electronic device in accordance with examples as disclosed herein.

DETAILED DESCRIPTION

A device, such as an electronic device, may support a number of applications (e.g., that may be based on software, hardware operation, or some combination) that allow a user to monitor and manage various aspects of the user's life. For example, an electronic device may support an application (e.g., a grocery shopping application) that allows a user to execute one or more operations, such as virtually shop (e.g., buy grocery items online). However, due to the limitations of the application, the user may still be responsible for selecting items for the user and the user may not have items that are otherwise tailored to the user. For example, the user may be responsible for specifically selecting items, such as grocery items, that are tailored to the user. Selecting appropriate items, such as grocery items, that fit with various user-specific criteria, such as the user's unique health, fitness, dietary restrictions, medications, allergies, food sensitivities, and budget, among other aspects unique to the user, may be a complex task that is time consuming and burdensome.

According to the techniques described herein, an electronic device may be configured with an artificial intelligence (AI) application that uses AI techniques and processes to determine personalized criteria for a user, and in turn a personalized output (e.g., a list) that is based on the personalized criteria. In some examples, according to the techniques described herein, an electronic device may be configured with an artificial intelligence (AI) application, such as an AI nutrition application, that uses AI techniques to determine a first personalized output, such as a personalized diet for a user, and in turn a second personalized output, such as a grocery list that is based on the first personalized output. The AI application may interface with other applications to obtain user data (e.g., health data, diet data, medication data, allergy data, food sensitivity data, budget data) that the AI application can use as a basis for determining user-specific criteria for the personalized outputs, for the user. The AI application may apply user-specified weighting factors to different categories of the criteria so that the criteria are prioritized according to, among other aspects, the user's preferences.

Features of the disclosure are initially described in the context of systems and dies as described with reference to FIG. 1. Features of the disclosure are described in the context of an electronic device, an AI application, and a process flow as described with reference to FIGS. 2, 3, and 4, respectively. These and other features of the disclosure are further illustrated by and described with reference to an apparatus diagram and flowcharts that relate to an artificial intelligence system on an electronic device as described with reference to FIGS. 5-7.

Figure 1:
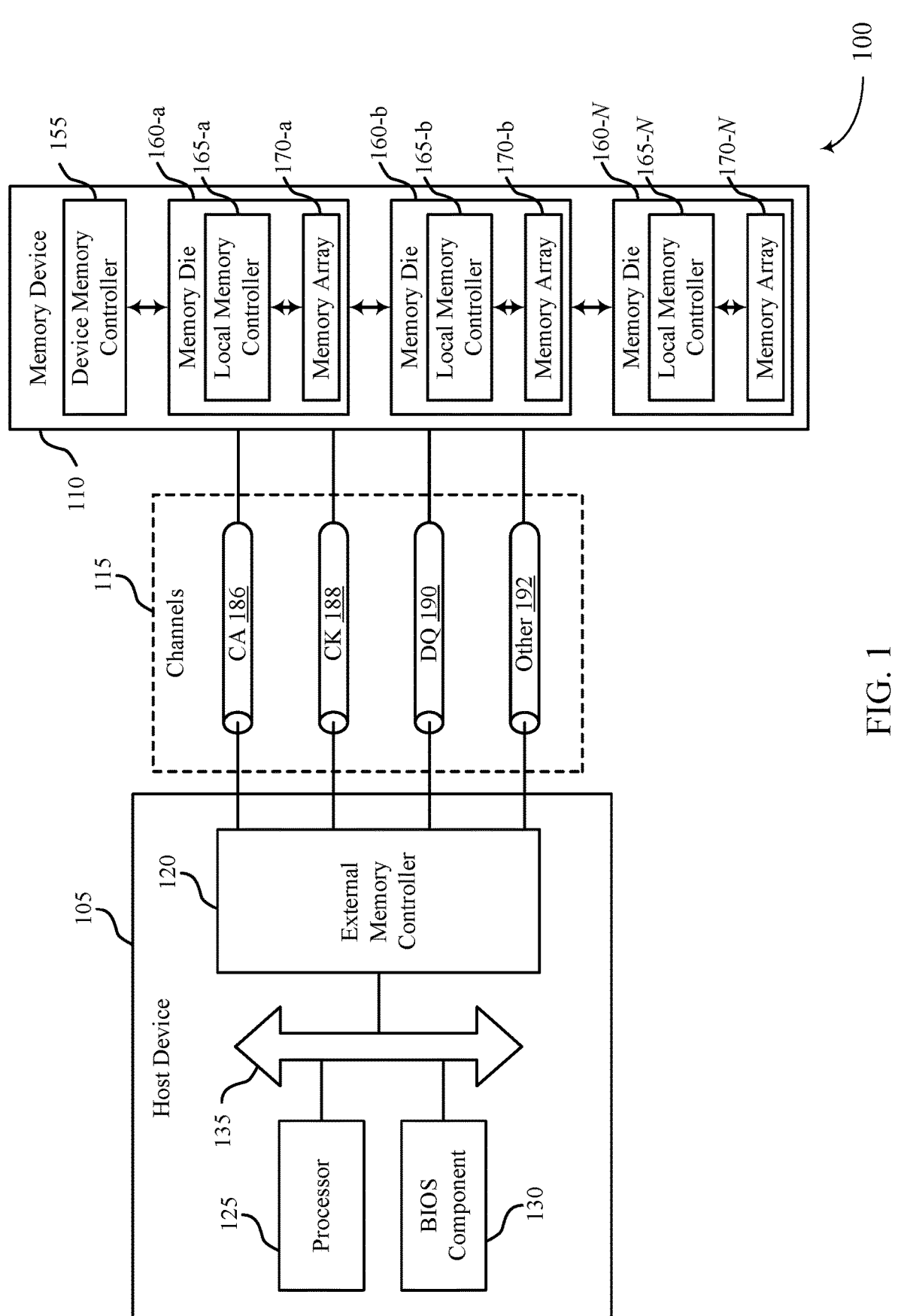
FIG. 1 illustrates an example of a system that supports an artificial intelligence system on an electronic device in accordance with examples as disclosed herein.

FIG. 1 illustrates an example of a system 100 that supports an artificial intelligence system on an electronic device in accordance with examples as disclosed herein. The system 100 may include a host device 105, a memory device 110, and a plurality of channels 115 coupling the host device 105 with the memory device 110. The system 100 may include one or more memory devices 110, but aspects of the one or more memory devices 110 may be described in the context of a single memory device (e.g., memory device 110).

The system 100 may include portions of an electronic device, such as a computing device, a mobile computing device, a wireless device, a graphics processing device, a vehicle, or other systems. For example, the system 100 may illustrate aspects of a computer, a laptop computer, a tablet computer, a smartphone, a cellular phone, a wearable device, an internet-connected device, a vehicle controller, or the like. The memory device 110 may be a component of the system operable to store data for one or more other components of the system 100.

At least portions of the system 100 may be examples of the host device 105. The host device 105 may be an example of a processor or other circuitry within a device that uses memory to execute processes (wherein such "other circuitry" is hereinafter also referred to in the specification and claims as a "processor"), such as within a computing device, a mobile computing device, a wireless device, a graphics processing device, a computer, a laptop computer, a tablet computer, a smartphone, a cellular phone, a wearable device, an internet-connected device, a vehicle controller, a system on a chip (SoC), or some other stationary or portable electronic device, among other examples. In some examples, the host device 105 may refer to the hardware, firmware, software, or any combination thereof that implements the functions of an external memory controller 120. In some examples, the external memory controller 120 may be referred to as a host (e.g., as host device 105).

A memory device 110 may be an independent device or a component that is operable to provide physical memory addresses/space that may be used or referenced by the system 100. In some examples, a memory device 110 may be configurable to work with one or more different types of host devices. Signaling between the host device 105 and the memory device 110 may be operable to support one or more of: modulation schemes to modulate the signals, various pin configurations for communicating the signals, various form factors for physical packaging of the host device 105 and the memory device 110, clock signaling and synchronization between the host device 105 and the memory device 110, timing conventions, or other factors.

The memory device 110 may be operable to store data for the components of the host device 105. In some examples, the memory device 110 may act as a secondary-type or dependent-type device to the host device 105 (e.g., responding to and executing commands provided by the host device 105 through the external memory controller 120). Such commands may include one or more of a write command for a write operation, a read command for a read operation, a refresh command for a refresh operation, or other commands.

The memory devices 110 may be an example of random access memory (RAM), read-only memory (ROM), dynamic RAM (DRAM), synchronous dynamic RAM (SDRAM), a static RAM (SRAM), ferroelectric RAM (Fe-RAM), magnetic RAM (MRAM), resistive RAM (RRAM), flash memory, phase change memory (PCM), self-selecting memory, chalcogenide memory, or not-or (NOR) and not-and (NAND) memory, among other examples. Thus, the memory cells of the memory device 100 may be volatile or non-volatile. Non-volatile memory devices (e.g., NAND memory), may maintain their stored logic state for extended periods of time even in the absence of an external power source. Volatile memory devices, e.g., DRAM, may lose their stored state when disconnected from an external power source.

The host device 105 may include one or more of an external memory controller 120, a processor 125, a basic input/output system (BIOS) component 130, or other components such as one or more peripheral components or one or more input/output controllers. The components of the host device 105 may be coupled with one another using a bus 135.

The processor 125 may be operable to provide control or other functionality for at least portions of the system 100 or at least portions of the host device 105. The processor 125 may be a general-purpose processor, a digital signal processor (DSP), an application-specific integrated circuit (ASIC), a field-programmable gate array (FPGA) or other programmable logic device, discrete gate or transistor logic, discrete hardware components, or a combination of these components. In such examples, the processor 125 may be an example of a central processing unit (CPU), a graphics processing unit (GPU), a general purpose GPU (GPGPU), or an SoC, among other examples. In some examples, the external memory controller 120 may be implemented by or be a part of the processor 125.

The BIOS component 130 may be a software component that includes a BIOS operated as firmware, which may initialize and run various hardware components of the system 100 or the host device 105. The BIOS component 130 may also manage data flow between the processor 125 and the various components of the system 100 or the host device 105. The BIOS component 130 may include a program or software stored in one or more of read-only memory (ROM), flash memory, or other non-volatile memory.

In some examples, the system 100 or the host device 105 may include an input component, an output component, or both. An input component may represent a device or signal external to the system 100 that provides information, signals, or data to the system 100 or its components. In some examples, and input component may include a user interface or interface with or between other devices. In some examples, an input component may be a peripheral that interfaces with system 100 via one or more peripheral components or may be managed by an I/O controller. An output component may represent a device or signal external to the system 100 operable to receive an output from the system 100 or any of its components. Examples of an output component may include a display, audio speakers, a printing device, another processor on a printed circuit board, and others. In some examples, an output may be a peripheral that interfaces with the system 100 via one or more peripheral components or may be managed by an I/O controller.

The memory device 110 may include a device memory controller 155 and one or more memory dies 160 (e.g., memory chips) to support a desired capacity or a specified capacity for data storage. Each memory die 160 (e.g., memory die 160-a, memory die 160-b, memory die 160-N) may include a local memory controller 165 (e.g., local memory controller 165-a, local memory controller 165-b, local memory controller 165-N) and a memory array 170 (e.g., memory array 170-a, memory array 170-b, memory array 170-N). A memory array 170 may be a collection (e.g., one or more grids, one or more banks, one or more tiles, one or more sections) of memory cells, with each memory cell being operable to store at least one bit of data. A memory device 110 including two or more memory dies 160 may be referred to as a multi-die memory or a multi-die package or a multi-chip memory or a multi-chip package.

The device memory controller 155 may include circuits, logic, or components operable to control operation of the memory device 110. The device memory controller 155 may include the hardware, the firmware, or the instructions that enable the memory device 110 to perform various operations and may be operable to receive, transmit, or execute commands, data, or control information related to the components of the memory device 110. The device memory controller 155 may be operable to communicate with one or more of the external memory controller 120, the one or more memory dies 160, or the processor 125. In some examples, the device memory controller 155 may control operation of the memory device 110 described herein in conjunction with the local memory controller 165 of the memory die 160.

A local memory controller 165 (e.g., local to a memory die 160) may include circuits, logic, or components operable to control operation of the memory die 160. In some examples, a local memory controller 165 may be operable to communicate (e.g., receive or transmit data or commands or both) with the device memory controller 155. In some examples, a memory device 110 may not include a device memory controller 155, and a local memory controller 165 or the external memory controller 120 may perform various functions described herein. As such, a local memory controller 165 may be operable to communicate with the device memory controller 155, with other local memory controllers 165, or directly with the external memory controller 120, or the processor 125, or any combination thereof. Examples of components that may be included in the device memory controller 155 or the local memory controllers 165 or both may include receivers for receiving signals (e.g., from the external memory controller 120), transmitters for transmitting signals (e.g., to the external memory controller 120), decoders for decoding or demodulating received signals, encoders for encoding or modulating signals to be transmitted, or various other circuits or controllers operable for supporting described operations of the device memory controller 155 or local memory controller 165 or both.

The external memory controller 120 may be operable to enable communication of one or more of information, data, or commands between components of the system 100 or the host device 105 (e.g., the processor 125) and the memory device 110. The external memory controller 120 may convert or translate communications exchanged between the components of the host device 105 and the memory device 110. In some examples, the external memory controller 120 or other component of the system 100 or the host device 105, or its functions described herein, may be implemented by the processor 125. For example, the external memory controller 120 may be hardware, firmware, or software, or some combination thereof implemented by the processor 125 or other component of the system 100 or the host device 105. Although the external memory controller 120 is depicted as being external to the memory device 110, in some examples, the external memory controller 120, or its functions described herein, may be implemented by one or more components of a memory device 110 (e.g., a device memory controller 155, a local memory controller 165) or vice versa.

The components of the host device 105 may exchange information with the memory device 110 using one or more channels 115. The channels 115 may be operable to support communications between the external memory controller 120 and the memory device 110. Each channel 115 may be examples of transmission mediums that carry information between the host device 105 and the memory device. Each channel 115 may include one or more signal paths or transmission mediums (e.g., conductors) between terminals associated with the components of the system 100. A signal path may be an example of a conductive path operable to carry a signal. For example, a channel 115 may include a first terminal including one or more pins or pads at the host device 105 and one or more pins or pads at the memory device 110. A pin may be an example of a conductive input or output point of a device of the system 100, and a pin may be operable to act as part of a channel.

Channels 115 (and associated signal paths and terminals) may be dedicated to communicating one or more types of information. For example, the channels 115 may include one or more command and address (CA) channels 186, one or more clock signal (CK) channels 188, one or more data (DQ) channels 190, one or more other channels 192, or any combination thereof. In some examples, signaling may be communicated over the channels 115 using single data rate (SDR) signaling or double data rate (DDR) signaling. In SDR signaling, one modulation symbol (e.g., signal level) of a signal may be registered for each clock cycle (e.g., on a rising or falling edge of a clock signal). In DDR signaling, two modulation symbols (e.g., signal levels) of a signal may be registered for each clock cycle (e.g., on both a rising edge and a falling edge of a clock signal).

The memory device 110 may be configured to store algorithms and data for applications on the system 100. For example, the memory device 110 may be configured to store an algorithm and data for an AI nutrition application as described herein. The AI nutrition application may interface with other applications supported by the system 100 to, for example, obtain user data that the AI nutrition application uses to generate a personalized (e.g., custom, tailored, user-specific) diet, a personalized grocery list, or both, for a user. In some examples, the AI nutrition application may interface with the other applications to retrieve supporting information (e.g., ingredient lists, nutrition information, medication interaction information, supplement absorption information) that helps the AI nutrition application generate the personalized diet, the personalized grocery list, or both. Additionally or alternatively, the AI nutrition system may retrieve the supporting information from one or more sources (e.g., storage locations, databases) stored in the memory device 110, from a remote server (e.g., via the Internet), other sources, or any combination.

Figure 2:
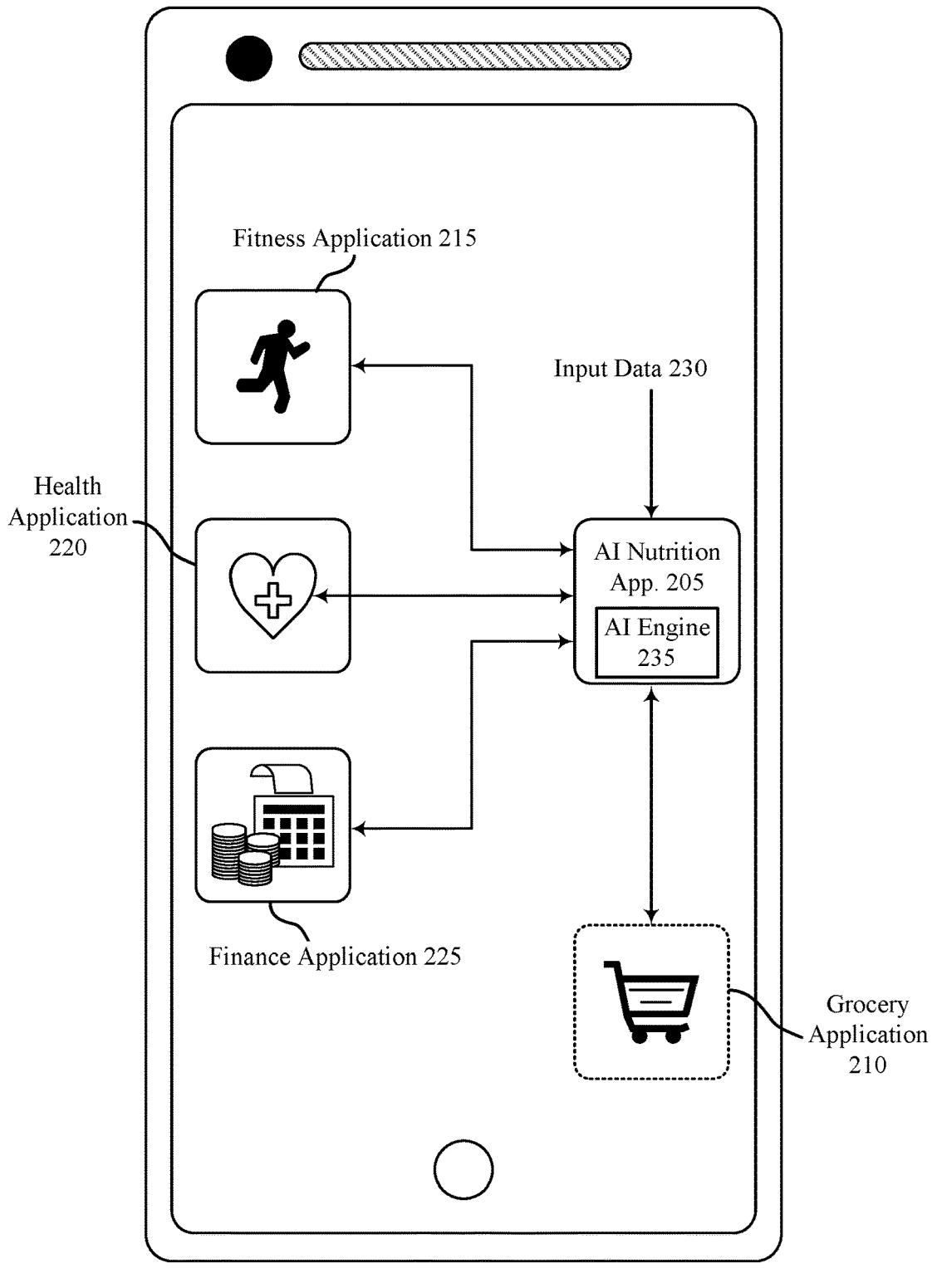
FIG. 2 illustrates an example of an electronic device that supports an artificial intelligence system on an electronic device in accordance with examples as disclosed herein.

FIG. 2 illustrates an example of an electronic device 200 that supports an artificial intelligence system on an electronic device in accordance with examples as disclosed herein. The electronic device 200 may be an example of, or include, the system 100 as described with reference to FIG. 1. Although FIG. 2 is described with application to various examples, including nutrition, the applicability is not limited to the examples provided and can be more broadly implemented in memory devices and related systems distinct from the examples provided. The electronic device 200 may be configured with an AI nutrition application 205 (e.g., that may be based on software, hardware operation, or some combination) as discussed herein. Although depicted and described as a standalone application, the AI nutrition application 205 may be implemented as an end solution that is part of another application (e.g., the grocery application 210). Alternatively, the AI nutrition application may be a transparent algorithm that runs in the background while the electronic device 200 performs other operations.

In addition to the AI nutrition application 205, the electronic device 200 may be configured with a quantity of other applications. For example, the electronic device 200 may include a fitness application 215, a health application 220, a finance application 225, the grocery application 210, or any combination thereof. The fitness application 215 may maintain, provide access to, or both, one or more databases of user fitness data, the health application 220 may maintain, provide access to, or both, one or more databases of user health data, and the finance application 225 may maintain, provide access to, or both, one or more databases of user financial data. The grocery application 210 may provide access to an online grocery shopping system. Although described with reference to several specific applications, the electronic device 200 may support fewer, additional, and/or different types of applications. Although shown separate from the grocery application 210, the AI nutrition application 205 may include one or more other applications, such as the grocery application 210 or provide the functionality of the grocery application 210 (e.g., the AI nutrition application 205 may encompass or perform the functions of the grocery application 210).

The AI nutrition application 205 may communicate with other applications on the electronic device 200 to obtain user data that the AI nutrition application 205 is configured to use as a basis for generating a personalized diet for the user. For example, the AI nutrition application 205 may communicate with the fitness application 215 to obtain fitness information (e.g., minutes of exercise a day, types of exercise) for the user. Additionally or alternatively, the AI nutrition application 205 may communicate with the health application 220 to obtain health information (e.g., medical conditions, biometrics, prescriptions, allergies, food sensitivities) for the user. Additionally or alternatively, the AI nutrition application 205 may communicate with the finance application 225 to obtain financial information for the user (e.g., bank account balance, income, monthly expenditures).

The AI nutrition application 205 may be configured to use the user data to determine criteria for generating a personalized diet (and/or a personalized grocery list) for the user. The criteria may, in some examples, be divided into different categories, such as medication-based criteria (e.g., criteria that depend on user medications), allergy-based criteria (e.g., criteria that depend on user allergies), food sensitivity-based criteria (e.g., criteria that depend on user food-sensitivities), diet-based criteria (e.g., criteria that depend on user diet), health-based criteria (e.g., criteria that depend on user health conditions), fitness-based criteria (e.g., criteria that depend on user fitness), budget-based criteria (e.g., criteria that depend on user finances), or any combination thereof, among other examples. Criteria that depends on x may also be referred to as being a function of x. The AI nutrition application 205 may use the criteria to perform various operations, determinations, or both, such as to filter out foods and grocery items for the personalized diet and grocery list, respectively.

As an example of a medication-based criterion, if the user data includes medication information that indicates that the user is on Medication A (e.g., statins), the AI nutrition application 205 may determine that the personalized diet should exclude foods that negatively interact with Medication A (or should include foods that positively interact with Medication A, or some combination thereof). In some examples, the AI nutrition application 205 may use medication information to infer one or more health conditions that the AI nutrition application 205 can use as health information for determining health-based criteria. As an example of an allergy-based criterion, if the user data includes allergy information that indicates the user is allergic to substance B (e.g., lactose), the AI nutrition application 205 may determine that the personalized diet should exclude foods that include substance B. As an example of a food-sensitivity based criterion, if the user data includes food-sensitivity information that indicates the user has a sensitivity to substance C (e.g., gluten), the AI nutrition application 205 may determine that personalized diet should exclude foods with any gluten or foods with a threshold level of gluten.

As an example of a diet-based criterion, if the user data includes diet information that indicates the user is following a low carbohydrate diet, the AI nutrition application 205 may determine that the personalized diet should exclude foods with a threshold level of carbohydrates. As an example of a health-based criterion, if the user data includes health information that indicates the user has health condition D, the AI nutrition application 205 may determine that the personalized diet should exclude foods that exacerbate health condition D. As an example of a fitness-based criterion, if the user data includes fitness information that indicates the activity level of the user is low, the AI nutrition application 205 may determine that the personalized diet should exclude high calorie foods (e.g., foods with calories above a threshold level). As an example of a budget-based criterion, if the user data includes financial information that indicates a budget of the user, the AI nutrition application 205 may determine that the personalized diet should exclude foods that have a cost above a threshold.

The AI nutrition application 205 may determine which foods satisfy a criterion by communicating with another application (e.g., health application 220), by accessing a data based stored on a memory of the electronic device 200, by accessing a remote server (e.g., via the Internet), or any combination thereof.

In addition to receiving user data from one or more applications, the AI nutrition application 205 may be configured to receive input data 230 (e.g., a scanned prescription) that may be provided by the user (e.g., can be manually provided by the user), another source (e.g., a healthcare professional such as a doctor or a pharmacist), or any combination thereof. The input data 230 may include user data, an indication of priority levels for the categories of criteria, other information, or some combination thereof. For example, the input data 230 may indicate various priority levels for the different categories of criteria. Each priority level may be associated with a respective weighting factor that the AI nutrition application 205 applies to the category assigned that priority level. Alternatively, the input data 230 may indicate the priority levels indirectly by indicating the weighting factors for the categories, where higher weighting factors correspond to higher priority levels.

The AI nutrition application 205 may use the user data-based criteria to determine a personalized diet (a list of recommended foods) for the user. For example, the AI nutrition application 205 may include an AI engine 235 that uses various determinations and operations, including artificial intelligence (e.g., machine learning), to determine the personalized diet for the user. As noted, the AI engine 235 may be configured to assign the criteria to various categories and apply weighting factors to the criteria to further tailor the personalized diet to the user. The weighting factors applied to the categories of user information may be default weighting factors, learned weighting factors, or weighting factors provided by the user (e.g., via the input data 230), or any combination thereof.

After determining the personalized diet for the user, the AI nutrition application 205 may display the personalized diet, communicate the personalized diet to the grocery application 210, or both. If the AI nutrition application 205 is included in or extends to the grocery application 210, the AI nutrition application 205 may use the personalized diet to determine a personalized grocery list for the user. For example, the AI nutrition application 205 may use the personalized diet to select a set of grocery items for the user to buy. Some or all of the criteria for the personalized diet may also apply to the personalized grocery list. After the personalized grocery list is determined, the AI nutrition application 205 (or the grocery application 210) may output the grocery list. For example, the AI nutrition application 205 may display the grocery list for review by the user, communicate the grocery list to the grocery application 210, or both.

Figure 3:
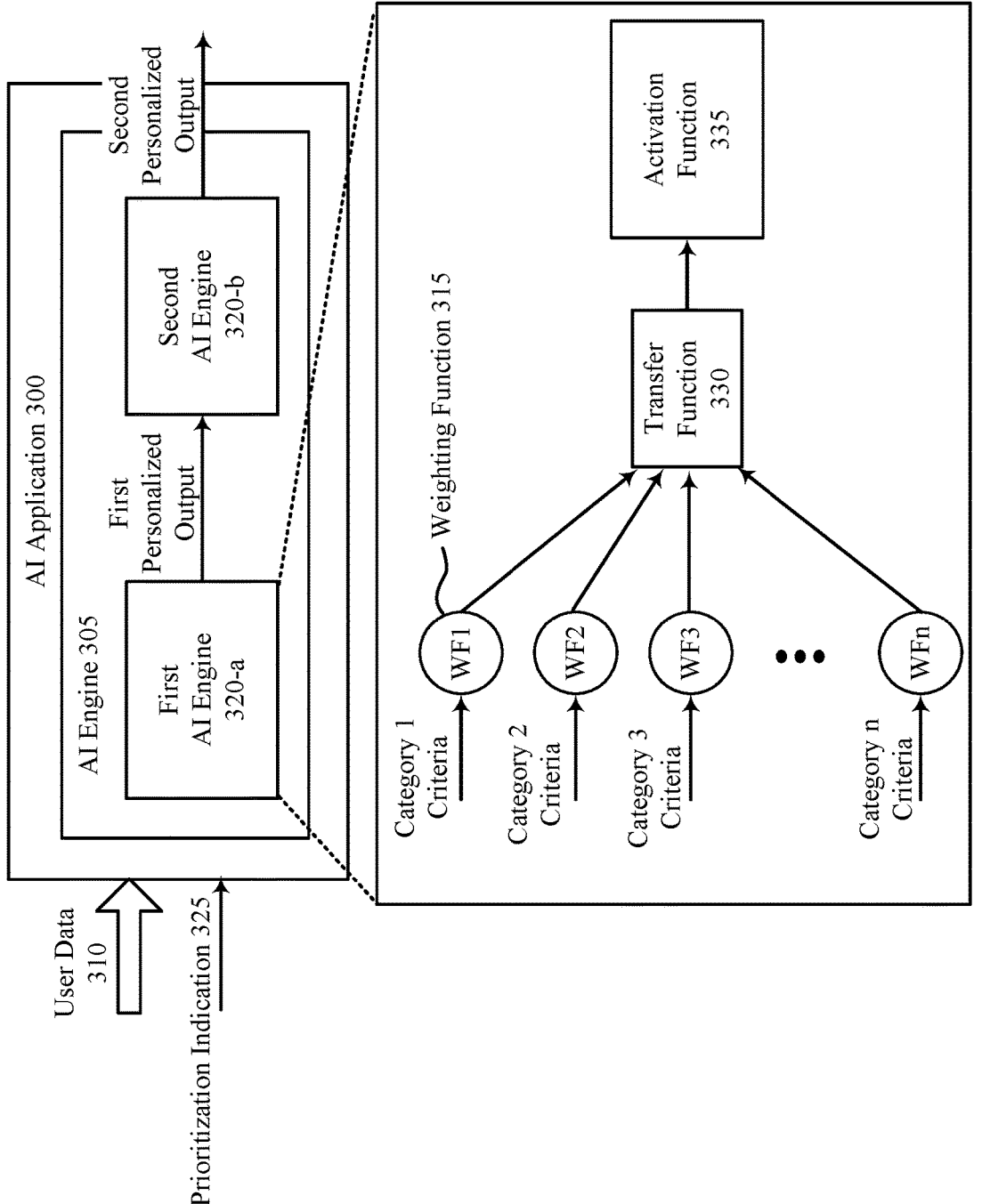
FIG. 3 illustrates an example of an artificial intelligence application in accordance with examples as disclosed herein.

FIG. 3 illustrates an example of an AI application 300 that supports an artificial intelligence system on an electronic device in accordance with examples as disclosed herein. Although FIG. 3 is described with application to various examples, including nutrition, the applicability is not limited to the examples provided and can be more broadly implemented in memory devices and related systems distinct from the examples provided. The AI nutrition application 205 described with reference to FIG. 2 may be an example of the AI application 300. The AI application 300 may receive user data 310 and use the user data 310 to determine one or more outputs that are personalized to the user of the electronic device that includes the AI application 300. In some examples, the user data 310 may include medication information, allergy information, food sensitivity information, diet information, health information, fitness information, budget information, or any combination thereof, among other types of data. The user data 310 may include user data received from one or more applications on the electric device that includes the AI application 300. Additionally or alternatively, the user data 310 may include user data input by the user.

The AI application 300 may use the user data 310 to determine criteria that the AI application 300 divides into different categories of criteria. For example, the AI application 300 may use the user data 310 to determine medication-based criteria, allergy-based criteria, food sensitivity-based criteria, diet-based criteria, health-based criteria, fitness-based criteria, budget-based criteria, or any combination thereof. The AI application 300 may divide the criteria into different categories so that the AI engines 320 can prioritize the categories (e.g., by applying different weights to the different categories) according to the preferences of the user.

The AI application 300 may include an AI engine 305 that includes one or multiple AI engines 320 configured to generate one or more personalized outputs (e.g., lists) for a user. For example, the AI engine 305 may include a first AI engine 320-a that is configured to generate a first personalized output for the user and a second AI engine 320-b that is configured to generate a second personalized output for the user. More specifically, in some examples, the first AI engine 320-a may be configured to generate a personalized diet for the user and the second AI engine 320-b may be configured to generate a personalized grocery list for the user. The first personalized output (e.g., the personalized diet) may be based on the criteria that the AI application 300 determined using the user data 310. The second personalized output (e.g., the personalized grocery list) may be based on the first personalized output (e.g., the personalized diet) and criteria that the AI application 300 determined using the user data 310.

Each AI engine 320 may be configured to apply weighting factors to the categories of criteria in accordance with prioritization levels for the categories. For example, the AI engine 320-a may include one or more weighting functions 315, which may apply weighting factors (e.g., multipliers) to different categories of criteria, which may also be referred to as features. To illustrate, the weighting function WF1 may apply a first weighting factor to a first category of criteria (e.g., health-based criteria), the weighting function WF2 may apply a second weighting factor to a second category of criteria (e.g., allergy-based criteria), the weighting function WF3 may apply a third weighting factor to a third category of criteria (e.g., diet-based criteria), and so on and so forth. For example, one or more AI engines 320 may configured to determine and apply a first weighting factor (which may be given a weight of 2.0 or 2X), a second weighting factor (which may be given a weight of 1.5 or 1.5X or 1.3, or 1.3X), and a third weighting factor (which may be given a weight of 1.0 or 1X), where X may be a baseline weighting factor or a default weighting factor. The AI engine 320-b may be configured similar to the AI engine 320-a.

The weighting factors applied to the categories of information may be default weighting factors, determined by the AI application 300, selected by the user (e.g., via the prioritization indication 325), or any combination thereof. For example, the weighting factors may be learned (e.g., via machine learning) by the AI application 300. In some examples, the weighting factors may be default values that the user, or the AI application 300, can update to prioritize certain categories of criteria over other categories of criteria. To illustrate, given a default weighting factor of 20% per category, the user may prioritize a first category of criteria (e.g., allergy-based criteria) by indicating to increase the weighting factor for the first category (e.g., generally, or by a specific weighting factor adjustment for example to be 35%) and may de-prioritize a second category of criteria (e.g., fitness-based criteria) by indicating to decrease the weighting factor for the second category (e.g., generally, or by a specific weighting factor adjustment for example to be 5%). The AI application 300 may determine the prioritization level for a category based on an indication (e.g., the prioritization indication 325) received from the user.

In some examples, the AI application 300 may use the user data 310 to determine initial weighting factors for the categories of criteria. For example, if the user data 310 indicates that the user has a health condition (e.g., diabetes) that is greatly affected by diet, the AI application 300 may select a weighting factor for health-based criteria that prioritizes the health-based criteria over other categories of criteria. As another example, if the user data 310 indicates that the user is struggling financially (e.g., has a net worth below a threshold, has an income below a threshold), the AI application 300 may select a weighting factor for budget-based criteria that prioritizes the budget-based criteria over other categories of criteria. In some examples, the AI application 300 may use the user data 310 to adjust the weighting factors. For example, if the user data 310 indicates that the user has improved finances, the AI application 300 may deprioritize the budget-based criteria by reducing the weighting factor for the budget-based criteria.

In some examples, the AI application 300 may determine one or more of the weighting factors based on shopping trends of the user (e.g., based on foods and grocery items previously bought by the user). For example, the AI application 300 may determine that the foods and grocery items frequently bought by a user satisfy more criteria in first category than a second criteria. Accordingly, the AI application 300 may adjust the weighting factors applied to the first category and the second category so that the first category is prioritized more than the second category. In some examples, the AI application 300 may determine one or more of the weighting factors based on season. For example, the AI application 300 may use a first set of weighting factors for one season (e.g., summer) and second set of weighting factors for another season (e.g., winter). In some examples, the AI application 300 may intermittently (e.g., aperiodically or periodically) adjust the weighting factors based on feedback from the user. For example, the AI application 300 may select an initial value for a weighting factor for a category of criteria, then adjust the weighting factor to another value based on the user indicating a lower or higher priority for the category.

In some examples, the AI application 300 may determine and store different sets of weighting factors for different modes. For example, the AI application 300 may store a first set of weighting factors for a weight loss mode, may store a second set of weighting factors for a maintenance mode, may store a third set of weighting factors for a vacation mode, may store a fourth set of factors for a marathon mode, and the like. The AI application 300 may determine which set of weighting factors to apply categories of criteria based on an indication from the user that indicates the mode desired by the user.

After appropriately weighting the various categories of criteria, an AI engine 320 may pass the weighted information to a transfer function 330 for summation. After summing the weighted categories of criteria, the AI engine 320 may pass the result of the summation to an activation function 335, which may operate on the weighted categories to determine a personalized output for the user. The AI engine 320 may then output the personalized output. For example, the first AI engine 320-*a* may output a first personalized output (e.g., the personalized diet) to the second AI engine 320-*b*, and the second AI engine 320-*b* may output a second personalized output (e.g., the personalized grocery list) for display or for communication to another application (e.g., a grocery shopping application).

Figure 4:
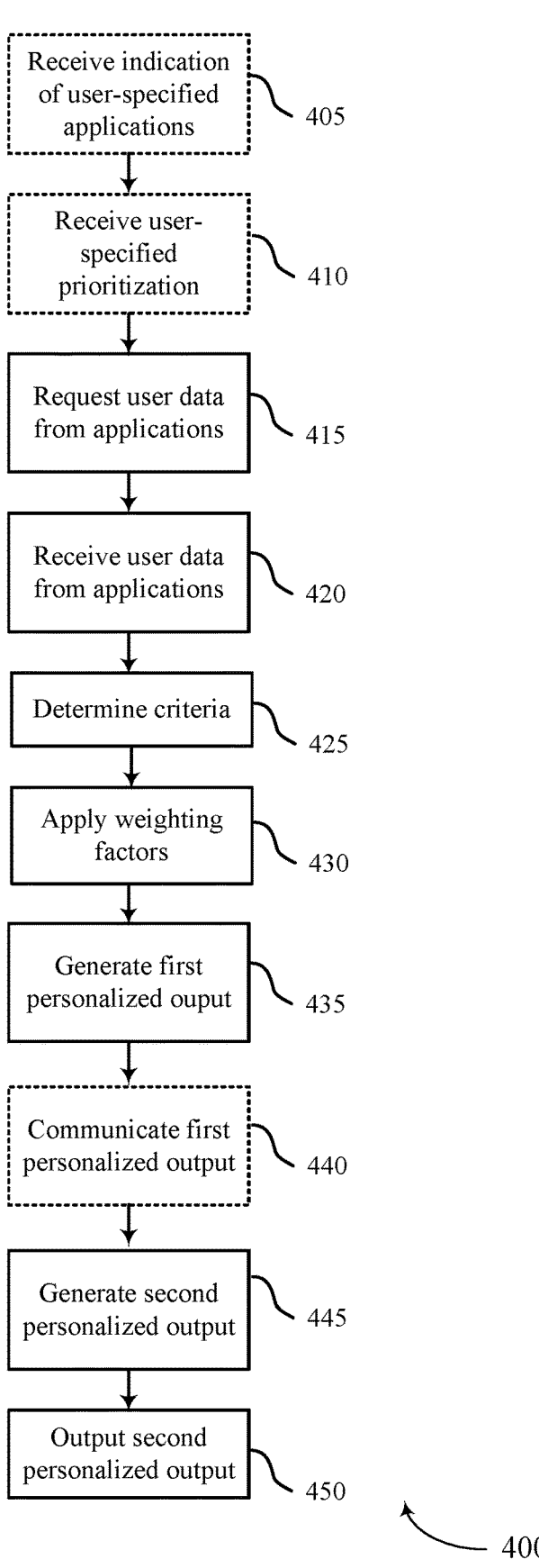
FIG. 4 illustrates an example of a process flow that supports an artificial intelligence system on an electronic device in accordance with examples as disclosed herein.

FIG. 4 illustrates an example of a process flow 400 that supports an artificial intelligence system on an electronic device in accordance with examples as disclosed herein. Although FIG. 4 is described with application to various examples, including nutrition, the applicability is not limited to the examples provided and can be more broadly implemented in memory devices and related systems distinct from the examples provided. The process flow 400 may be implemented by an electronic device that includes an AI application, such as an AI nutritional application, as described herein.

At 405, the AI application may receive (e.g., as input data 230) an indication of a set of user-specified applications with which an application, such as an AI application, is permitted to interface. For example, the user may indicate that the AI application is permitted to interface with first fitness application but not a second fitness application. At 405, the AI application may receive (e.g., as input data 230) an indication of user-specified priority levels for various categories (e.g., types, classes) of criteria. For example, the AI application may receive an indication of a first priority level for a first category of criteria (e.g., medication-based criteria), an indication of a second priority level for a second category of criteria (e.g., allergy-based criteria), and so on and so forth.

A user may indicate the priority level for a category by selecting a priority level for the user information. Each priority level may have an associated weighting factor. For example, a first priority level (e.g., level 1) may be associated with a first weighting factor (e.g., 35%), a second priority level (e.g., level 2) may be associated with a second lower weighting factor (e.g., 20%), and so on and so forth. Alternatively, the user may indicate the priority level for a category by selecting a specific weighting factor to be applied to the category. Higher weighting factors may be associated with higher priority levels. For example, the highest weighting factor selected by the user may be associated with the highest priority level, the second highest weighting factor selected by the user may be associated the second highest priority level, and so on and so forth. If a user does not indicate priority level for a certain category of user information, the electronic device may assign a default priority level with default weighting factor.

At 415, the AI application may request user data from one or more sources, such as one or more applications. For example, the electronic device may send a message requesting user data to the set of user-specified applications indicated by the user at 405. At 420, in response to the request(s)

at 415, the AI application may receive user data from the one or more applications. The user data may include medication information, allergy information, food sensitivity information, diet information, health information, fitness information, budget information, or any combination thereof, among other types of user data.

Medication information may be information that indicates a medication (e.g., prescription drug, an over-the-counter drug) that the user is on. The medication information may be information provided by user (e.g., manually provided by the user), another source (e.g., a healthcare professional such as a doctor or a pharmacist), or any combination thereof. Allergy information may be information that indicates an allergy (e.g. a food allergy) of the user. Food sensitivity information be information that indicates a food sensitivity of the user. Diet information may be information that indicates a type of diet of the user (e.g., a low-carb diet, a Pescatarian diet), diet restrictions for the user (e.g., food items with a threshold amount of trans fats), and the like. Health information may be information that indicates health conditions (e.g., illnesses, imbalances, deficiencies) of the user. Fitness information may be information that indicates aspects of the user's fitness, such as their weekly exercise routine, their daily activity, and the like. Budget information may be information that indicates aspects of the user's financial circumstances.

At 425, the AI application may determine criteria for one or more personalized outputs. For example, the AI application may determine criteria for a personalized diet, criteria for a personalized grocery list, or both. The AI application may determine the criteria based on the user data received at 415. For example, if the data includes medication information that indicates the user takes a particular medication, the AI application may determine a medication-based criterion that limits the foods in the personalized diet to those that safely interact with the medication. As another example, if the user data includes allergy information that indicates the user is allergic to a substance (e.g., soy), the AI application may determine an allergy-based criteria that filters out foods and grocery items with threshold amounts of the substance. As another example, if the user data includes health information that indicates the user is diabetic, the AI application may determine a health-based criterion that limits the amount of sugar in the personalized diet. As another example, if the user data includes budget information that indicates the budget of the user, the AI application may determine a budget-based criterion that limits the expense of each item for the personalized grocery list.

At 430, the AI application may apply weighting factors to the categories of criteria. The weighting factors may be the weighting factors associated with the priority levels indicated by the user at 410. Alternatively, the weighting factors may be the weighting factors selected by the user at 410. In some examples, the AI application may determine the weighting factors based on the user data received at 415. For example, the AI application may use the user data to determine a first weighting factor for a first category of criteria, a second weighting factor for a second category of criteria, and so on and so forth. In some examples, the AI application may determine sets of weighting factors for different modes, where each set of weighting factors is associated with a different mode.

At 435, the AI application may use AI techniques (e.g., machine learning) to generate a first personalized output (e.g., a personalized diet) for the user. For example, the AI application may use the weighted categories of criteria, information from previously generated personalized outputs, and feedback from the user to generate the first personalized output. Generating the personalized diet may include selecting foods for the personalized diet. In some examples, the AI application may generate the personalized diet based on the user data received at 420 and the criteria determined at 425. The personalized diet may also be based on user data that is input by the user into the electronic device.

In some examples, the AI application may determine foods to include in (and items to exclude from) the personalized diet based on food-specific information obtained by the AI application. The AI application may obtain the food-specific information from one or more applications on the electronic device, from a database stored in a memory of the electronic device, from a remote server (e.g., via the Internet), from the user, or using a combination of these techniques. The AI application may use the food-specific information to determine whether a food satisfies various criteria for the personalized diet. For example, the food-specific information may include nutrition information, medication interaction information, supplement interaction information, and the like.

Nutrition information may refer to information related to the nutritional makeup of a food. For example, nutrition information may indicate the macronutrients in a food (e.g., the amount of carbohydrates, the amount of protein, the amount of fat, etc.), the vitamin makeup of the food, the mineral makeup of the food, and the like. Thus, the AI application may use nutrition information to select foods for the personalized diet for the user. For example, given a diet-based criterion that that limits the amount of sodium for the personalized diet, the AI application may determine whether to include a food in the personalized diet based on the sodium content of the food as indicated by the nutrition information.

Medication interaction information may refer to information that indicates how a food interacts with a medication. For example, medication interaction information may indicate that a particular food (e.g., grapefruit juice) dangerously interacts with a medication (e.g., statins). Thus, the AI application may use medication interaction information to avoid dangerous combinations of foods and drugs (e.g., in accordance with medication-based criteria). Put another way, the AI application may determine the personalized diet for the user based on the interaction properties of foods as indicated by medication interaction information for the foods.

Absorption information may refer to information that indicates how a supplement (e.g., a vitamin, a mineral) is absorbed by the body. For example, absorption information may indicate an element or substance enhances or inhibits absorption of a supplement. Thus, the AI application may use absorption information to promote supplement absorption (e.g., in accordance with health-based criteria). Put another way, the AI application may determine the personalized diet for the user based on the absorption enhancement and absorption inhibition properties of foods as indicated by absorption information for the foods.

The AI application may include a food in the personalized diet if the food satisfies all the criteria determined at 425 or if the food satisfies a threshold amount of high-priority criteria. For example, if a food fails to satisfy some criteria of a first category but satisfies a threshold amount of criteria of a second category, the AI application may include the food in the personalized diet if the second category has a higher priority level than the first category.

After determining the personalized diet, the AI application may display (e.g., using a graphical user interface (GUI)) the personalized diet for review by the user. The AI application may also store the personalized diet in memory (e.g., a memory die 160) for later access. At 440, the AI application may communicate the first personalized output (e.g., the personalized diet) to another AI engine of the AI application (e.g., the AI engine 320-*b*) or to a second application (e.g., a grocery shopping application, which may be configured with the AI engine 320-*b*).

At 445, the AI application may use AI techniques (e.g., machine learning) to generate a second personalized output (e.g., a personalized grocery list) for the user. For example, the AI application may use the weighted categories of criteria, information from previously generated personalized outputs, and feedback from the user to generate the second personalized output. Generating the personalized grocery list may include selecting food items for the personalized grocery list. In some examples, the AI application may generate the personalized grocery list based on the first personalized output (e.g., the personalized diet). The personalized grocery list may also be based on some or all of the criteria determined at 425. Additionally or alternatively, the AI application may use historical grocery shopping information as a basis for the personalized grocery list. For example, the AI application may receive one or more lists of grocery items that the user previously bought and may use the list of grocery items as a basis for including or excluding food items from the personalized grocery list determined at 445.

The AI application may include a food item in the personalized grocery list if the food items satisfies all the criteria determined at 425 or if the food item satisfies a threshold amount of high-priority criteria. For example, if a food items fails to satisfy some criteria of a first category but satisfies a threshold amount of criteria of a second category, the AI application may include the food items in the personalized diet if the second category has a higher priority level than the first category.

In some examples, the AI application may determine the personalized grocery list based on item-specific information obtained by the AI application. The AI application may obtain (e.g., retrieve) the item-specific information from one or more applications on the electronic device, from a database stored in a memory of the electronic device, from the user, from a remote server (e.g., via the Internet), or using a combination of these techniques. The AI application may use the food-specific information to determine whether an item satisfies various criteria for the personalized grocery list. For example, the item-specific information may include nutrition information, ingredient information, cost information, and the like.

Ingredient information may be information that indicates the ingredients of a grocery item. The AI application may use ingredient information to filter out grocery items for the personalized grocery list that do not satisfy various criteria determined at 425. Cost information may be information that indicates the cost of a grocery item. The AI application may use cost information to filter out grocery items for the personalized grocery list that do not satisfy budget-based criteria determined at 425. In some examples, the AI application may obtain one or more recipes (e.g., based on the personalized diet) and select grocery items for the grocery list based on the one or more recipes. At 450, the AI application may output the second personalized output (e.g., the personalized grocery list) to a grocery shopping application or to a GUI for display.

Thus, the AI application may generate personalized outputs (e.g., a personalized diet, a personalized grocery list) for a user based on user data.

Figure 5:
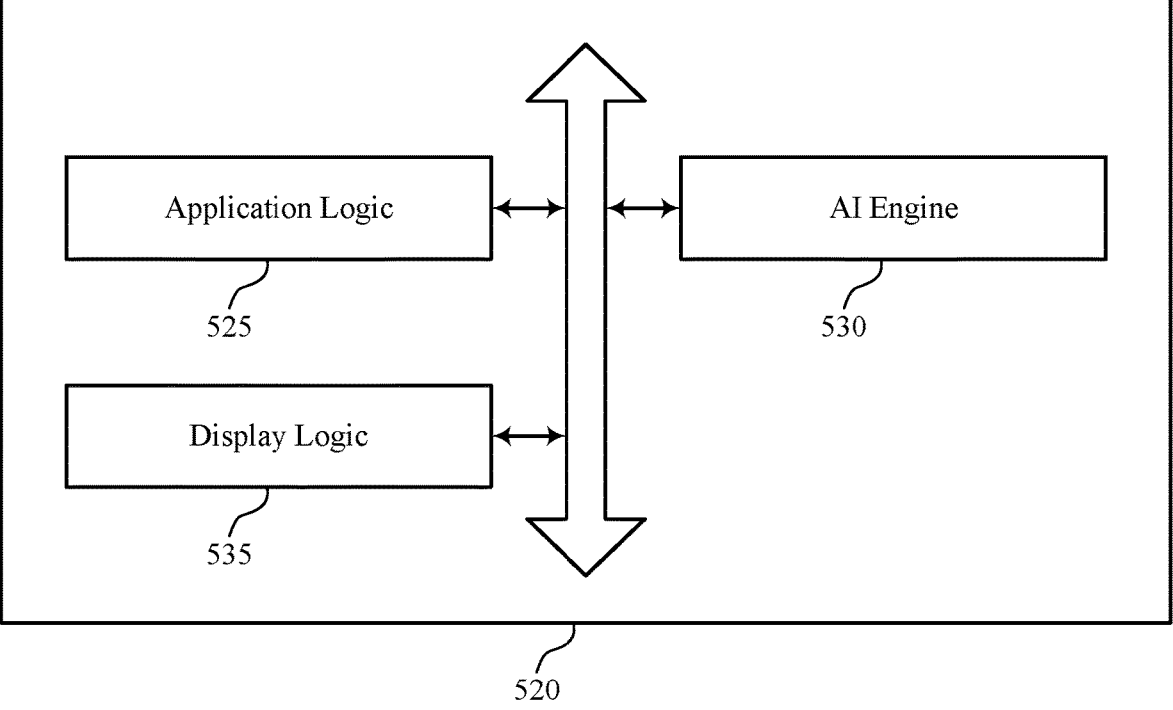
FIG. 5 shows a block diagram of an electronic device that supports an artificial intelligence system on an electronic device in accordance with examples as disclosed herein.

FIG. 5 shows a block diagram 500 of an electronic device 520 that supports an artificial intelligence system on an electronic device in accordance with examples as disclosed herein. The electronic device 520 may be an example of aspects of an electronic device as described with reference to FIGS. 1 through 4. The electronic device 520, or various components thereof, may be an example of means for performing various aspects of an artificial intelligence system on an electronic device as described herein. For example, the electronic device 520 may include an application logic 525, an AI engine 530, a display logic 535, or any combination thereof. Each of these components may communicate, directly or indirectly, with one another (e.g., via one or more buses).

The application logic 525 may be configured as or otherwise support a means for receiving, by a first application of the electronic device, user data for a user from the one or more applications of the electronic device. The AI engine 530 may be configured as or otherwise support a means for determining criteria for a personalized output for the user based at least in part on the user data. In some examples, the AI engine 530 may be configured as or otherwise support a means for determining, by an artificial intelligence engine of the first application, the personalized output for the user by applying weighting factors to the criteria, the weighting factors associated with priority levels for different categories of the criteria. In some examples, the AI engine 530 may be configured as or otherwise support a means for selecting, by the artificial intelligence engine of the first application, items for the user that are in accordance with the personalized output and that are based at least in part on the criteria for the personalized output and the priority levels for the different categories of the criteria. In some examples, the application logic 525 may be configured as or otherwise support a means for outputting a list of the items based at least in part on selecting the items.

In some examples, to support outputting the list of the items, the display logic 535 may be configured as or otherwise support a means for displaying the list of the items or communicating the list of the items to a second application.

In some examples, the application logic 525 may be configured as or otherwise support a means for receiving, from the user, an indication of a first priority level for a first category of the criteria. In some examples, the application logic 525 may be configured as or otherwise support a means for receiving, from the user, an indication of a second priority level for a second category of the criteria.

In some examples, the AI engine 530 may be configured as or otherwise support a means for determining a first weighting factor for the first category of criteria based at least in part on the first priority level for the first category. In some examples, the AI engine 530 may be configured as or otherwise support a means for determining a second weighting factor for the second category of criteria based at least in part on the second priority level for the second category, where applying the weighting factors includes applying the first weighting factor to the first category and applying the second weighting factor to the second category.

In some examples, the first priority level is higher than the second priority level, and the AI engine 530 may be configured as or otherwise support a means for determining that an item for the user satisfies the criteria for the first category but not the criteria for the second category; and where the selecting includes. In some examples, the first priority level is higher than the second priority level, and the AI engine 530 may be configured as or otherwise support a means for selecting the item for the user based at least in part on the first priority level for the first category being higher than the second priority level for the second category.

In some examples, the application logic 525 may be configured as or otherwise support a means for communicating, by the first application, a request for the user data to the one or more applications, where the user data is received based at least in part on communicating the request.

In some examples, the application logic 525 may be configured as or otherwise support a means for receiving, from the user, an indication that the first application is permitted to access the one or more applications, where the request is communicated to the one or more applications based at least in part on receiving the indication. In some examples, the personalized output includes a personalized diet and the items for the user include grocery items.

In some examples, the application logic 525 may be configured as or otherwise support a means for receiving, by a first application of the electronic device, user data associated with a user from one or more applications of the electronic device. In some examples, the AI engine 530 may be configured as or otherwise support a means for determining criteria for a personalized diet for the user based at least in part on the user data. In some examples, the AI engine 530 may be configured as or otherwise support a means for determining, by an artificial intelligence engine of the first application, the personalized diet for the user by applying weighting factors to the criteria, the weighting factors associated with priority levels for different categories of the criteria. In some examples, the AI engine 530 may be configured as or otherwise support a means for selecting, by the artificial intelligence engine of the first application, grocery items for the user that are in accordance with the personalized diet and that are based at least in part on the criteria for the personalized diet and the priority levels for the different categories of the criteria. In some examples, the application logic 525 may be configured as or otherwise support a means for outputting a list of the grocery items based at least in part on selecting the grocery items.

In some examples, to support outputting the list of the grocery items, the display logic 535 may be configured as or otherwise support a means for displaying the list of the grocery items or communicating the list of the grocery items to a grocery shopping application.

In some examples, to support receiving, the application logic 525 may be configured as or otherwise support a means for receiving, from the grocery shopping application, a second list of grocery items previously bought by the user, where the grocery items are selected based at least in part on the second list of grocery items.

In some examples, the application logic 525 may be configured as or otherwise support a means for receiving, from the user, an indication of the priority levels for the different categories of the criteria. In some examples, the AI engine 530 may be configured as or otherwise support a means for determining a budget for the user based at least in part on the user data, data input by the user, or both, where the grocery items are selected based at least in part on the budget.

In some examples, the application logic 525 may be configured as or otherwise support a means for receiving, from an application of the one or more applications, nutrition information for a set of foods, where the personalized diet is based at least in part on the nutrition information.

In some examples, the AI engine 530 may be configured as or otherwise support a means for determining, based at least in part on the received nutrition information, that a food of the set of foods satisfies at least some of the criteria for the personalized diet, where the food is included in the personalized diet based at least in part on determining that the food satisfies at least some of the criteria.

In some examples, to support determining that the food satisfies at least some of the criteria, the AI engine 530 may be configured as or otherwise support a means for determining that the food satisfies criteria of a first category but not criteria of a second category. In some examples, to support determining that the food satisfies at least some of the criteria, the AI engine 530 may be configured as or otherwise support a means for including the food in the personalized diet based at least in part on the first category having a higher priority than the second category.

In some examples, the application logic 525 may be configured as or otherwise support a means for receiving, from an application of the one or more applications, ingredient information for a set of grocery items, where the grocery items are selected based at least in part on the ingredient information.

In some examples, the AI engine 530 may be configured as or otherwise support a means for determining, based at least in part on the received ingredient information, that a grocery item of the set of grocery items satisfies at least some of the criteria for the personalized diet, where the grocery item is included in the list of the grocery items based at least in part on determining that the grocery item satisfies at least some of the criteria.

In some examples, to support determining that the grocery item satisfies at least some of the criteria, the AI engine 530 may be configured as or otherwise support a means for determining that the grocery item satisfies criteria of a first category but not criteria of a second category. In some examples, to support determining that the grocery item satisfies at least some of the criteria, the AI engine 530 may be configured as or otherwise support a means for including the grocery item in the list of the grocery items based at least in part on the first category having a higher priority than the second category.

In some examples, the user data includes allergy information for the user, and the AI engine 530 may be configured as or otherwise support a means for determining, based at least in part on the ingredient information and the allergy information, that the user is allergic to an ingredient in a grocery item of the set of grocery items; and where selecting the grocery items includes. In some examples, the user data includes allergy information for the user, and the AI engine 530 may be configured as or otherwise support a means for excluding the grocery item from the grocery items based at least in part determining that the user is allergic to the ingredient in the grocery item.

In some examples, the user data includes medication information that indicates a medication for the user, and the application logic 525 may be configured as or otherwise support a means for receiving, from an application of the one or more applications, an indication of an interaction between a food and the medication; and where determining the personalized diet includes. In some examples, the user data includes medication information that indicates a medication for the user, and the AI engine 530 may be configured as or otherwise support a means for excluding the food from the personalized diet based at least in part on the interaction.

In some examples, the user data includes medication information, allergy information, food sensitivity information, diet information, health information, fitness information, budget information, or any combination thereof. In some examples, the different categories of the criteria include medication-based criteria, allergy-based criteria, food sensitivity-based criteria, diet-based criteria, health-based criteria, fitness-based criteria, budget-based criteria, or any combination thereof.

FIG. 6 shows a flowchart illustrating a method 600 that supports an artificial intelligence system on an electronic device in accordance with examples as disclosed herein. The operations of method 600 may be implemented by an electronic device or its components as described herein. For example, the operations of method 600 may be performed by an electronic device as described with reference to FIGS. 1 through 5. In some examples, an electronic device may execute a set of instructions to control the functional elements of the device to perform the described functions. Additionally or alternatively, the electronic device may perform aspects of the described functions using special-purpose hardware.

At 605, the method may include receiving, by a first application of an electronic device, user data for a user from the one or more applications of the electronic device. The operations of 605 may be performed in accordance with examples as disclosed herein. In some examples, aspects of the operations of 605 may be performed by an application logic 525 as described with reference to FIG. 5.

At 610, the method may include determining criteria for a personalized output for the user based at least in part on the user data. The operations of 610 may be performed in accordance with examples as disclosed herein. In some examples, aspects of the operations of 610 may be performed by an AI engine 530 as described with reference to FIG. 5.

At 615, the method may include determining, by an artificial intelligence engine of the first application, the personalized output for the user by applying weighting factors to the criteria, the weighting factors associated with priority levels for different categories of the criteria. The operations of 615 may be performed in accordance with examples as disclosed herein. In some examples, aspects of the operations of 615 may be performed by an AI engine 530 as described with reference to FIG. 5.

At 620, the method may include selecting, by the artificial intelligence engine of the first application, items for the user that are in accordance with the personalized output and that are based at least in part on the criteria for the personalized output and the priority levels for the different categories of the criteria. The operations of 620 may be performed in accordance with examples as disclosed herein. In some examples, aspects of the operations of 620 may be performed by an AI engine 530 as described with reference to FIG. 5.

At 625, the method may include outputting a list of the items based at least in part on selecting the items. The operations of 625 may be performed in accordance with examples as disclosed herein. In some examples, aspects of the operations of 625 may be performed by an application logic 525 as described with reference to FIG. 5.

In some examples, an apparatus as described herein may perform a method or methods, such as the method 600. The apparatus may include, features, circuitry, logic, means, or instructions (e.g., a non-transitory computer-readable medium storing instructions executable by a processor), or any combination thereof for performing the following aspects of the present disclosure:

Aspect 1: The apparatus, including features, circuitry, logic, means, or instructions, or any combination thereof for receiving, by a first application of the electronic device, user data for a user from the one or more applications of the electronic device; determining criteria for a personalized output for the user based at least in part on the user data; determining, by an artificial intelligence engine of the first application, the personalized output for the user by applying weighting factors to the criteria, the weighting factors associated with priority levels for different categories of the criteria; selecting, by the artificial intelligence engine of the first application, items for the user that are in accordance with the personalized output and that are based at least in part on the criteria for the personalized output and the priority levels for the different categories of the criteria; and outputting a list of the items based at least in part on selecting the items.

Aspect 2: The apparatus of aspect 1 where outputting the list of the items, further includes operations, features, circuitry, logic, means, or instructions, or any combination thereof for displaying the list of the items or communicating the list of the items to a second application.

Aspect 3: The apparatus of any of aspects 1 through 2, further including operations, features, circuitry, logic, means, or instructions, or any combination thereof for receiving, from the user, an indication of a first priority level for a first category of the criteria and receiving, from the user, an indication of a second priority level for a second category of the criteria.

Aspect 4: The apparatus of aspect 3, further including operations, features, circuitry, logic, means, or instructions, or any combination thereof for determining a first weighting factor for the first category of criteria based at least in part on the first priority level for the first category and determining a second weighting factor for the second category of criteria based at least in part on the second priority level for the second category, where applying the weighting factors includes applying the first weighting factor to the first category and applying the second weighting factor to the second category.

Aspect 5: The apparatus of any of aspects 3 through 4 where the first priority level is higher than the second priority level and the method, apparatuses, and non-transitory computer-readable medium, further includes operations, features, circuitry, logic, means, or instructions, or any combination thereof for determining that an item for the user satisfies the criteria for the first category but not the criteria for the second category; and where the selecting includes and selecting the item for the user based at least in part on the first priority level for the first category being higher than the second priority level for the second category.

Aspect 6: The apparatus of any of aspects 1 through 5, further including operations, features, circuitry, logic, means, or instructions, or any combination thereof for communicating, by the first application, a request for the user data to the one or more applications, where the user data is received based at least in part on communicating the request.

Aspect 7: The apparatus of aspect 6, further including operations, features, circuitry, logic, means, or instructions, or any combination thereof for receiving, from the user, an indication that the first application is permitted to access the one or more applications, where the request is communicated to the one or more applications based at least in part on receiving the indication.

Aspect 8: The apparatus of any of aspects 1 through 7, further including operations, features, circuitry, logic, means, or instructions, or any combination thereof for the personalized output includes a personalized diet and the items for the user include grocery items.

FIG. 7 shows a flowchart illustrating a method 700 that supports an artificial intelligence system on an electronic device in accordance with examples as disclosed herein. The operations of method 700 may be implemented by an electronic device or its components as described herein. For example, the operations of method 700 may be performed by an electronic device as described with reference to FIGS. 1 through 5. In some examples, an electronic device may execute a set of instructions to control the functional elements of the device to perform the described functions. Additionally or alternatively, the electronic device may perform aspects of the described functions using special-purpose hardware.

At 705, the method may include receiving, by a first application of an electronic device, user data associated with a user from one or more applications of the electronic device. The operations of 705 may be performed in accordance with examples as disclosed herein. In some examples, aspects of the operations of 705 may be performed by an application logic 525 as described with reference to FIG. 5.

At 710, the method may include determining criteria for a personalized diet for the user based at least in part on the user data. The operations of 710 may be performed in accordance with examples as disclosed herein. In some examples, aspects of the operations of 710 may be performed by an AI engine 530 as described with reference to FIG. 5.

At 715, the method may include determining, by an artificial intelligence engine of the first application, the personalized diet for the user by applying weighting factors to the criteria, the weighting factors associated with priority levels for different categories of the criteria. The operations of 715 may be performed in accordance with examples as disclosed herein. In some examples, aspects of the operations of 715 may be performed by an AI engine 530 as described with reference to FIG. 5.

At 720, the method may include selecting, by the artificial intelligence engine of the first application, grocery items for the user that are in accordance with the personalized diet and that are based at least in part on the criteria for the personalized diet and the priority levels for the different categories of the criteria. The operations of 720 may be performed in accordance with examples as disclosed herein. In some examples, aspects of the operations of 720 may be performed by an AI engine 530 as described with reference to FIG. 5.

At 725, the method may include outputting a list of the grocery items based at least in part on selecting the grocery items. The operations of 725 may be performed in accordance with examples as disclosed herein. In some examples, aspects of the operations of 725 may be performed by an application logic 525 as described with reference to FIG. 5.

In some examples, an apparatus as described herein may perform a method or methods, such as the method 700. The apparatus may include, features, circuitry, logic, means, or instructions (e.g., a non-transitory computer-readable medium storing instructions executable by a processor), or any combination thereof for performing the following aspects of the present disclosure:

Aspect 9: The apparatus, including features, circuitry, logic, means, or instructions, or any combination thereof for receiving, by a first application of the electronic device, user data associated with a user from one or more applications of the electronic device; determining criteria for a personalized diet for the user based at least in part on the user data; determining, by an artificial intelligence engine of the first application, the personalized diet for the user by applying weighting factors to the criteria, the weighting factors associated with priority levels for different categories of the criteria; selecting, by the artificial intelligence engine of the first application, grocery items for the user that are in accordance with the personalized diet and that are based at least in part on the criteria for the personalized diet and the priority levels for the different categories of the criteria; and outputting a list of the grocery items based at least in part on selecting the grocery items.

Aspect 10: The apparatus of aspect 9 where outputting the list of the grocery items, further includes operations, features, circuitry, logic, means, or instructions, or any combination thereof for displaying the list of the grocery items or communicating the list of the grocery items to a grocery shopping application.

Aspect 11: The apparatus of aspect 10 where receiving, further includes operations, features, circuitry, logic, means, or instructions, or any combination thereof for receiving, from the grocery shopping application, a second list of grocery items previously bought by the user, where the grocery items are selected based at least in part on the second list of grocery items.

Aspect 12: The apparatus of any of aspects 9 through 11, further including operations, features, circuitry, logic, means, or instructions, or any combination thereof for receiving, from the user, an indication of the priority levels for the different categories of the criteria.

Aspect 13: The apparatus of any of aspects 9 through 12, further including operations, features, circuitry, logic, means, or instructions, or any combination thereof for determining a budget for the user based at least in part on the user data, data input by the user, or both, where the grocery items are selected based at least in part on the budget.

Aspect 14: The apparatus of any of aspects 9 through 13, further including operations, features, circuitry, logic, means, or instructions, or any combination thereof for receiving nutrition information for a set of foods, where the personalized diet is based at least in part on the nutrition information. The nutrition information may be received from an application of the one or more application, from a memory included in the electronic device, from the user, from a remote server, or from any combination thereof.

Aspect 15: The apparatus of aspect 14, further including operations, features, circuitry, logic, means, or instructions, or any combination thereof for determining, based at least in part on the received nutrition information, that a food of the set of foods satisfies at least some of the criteria for the personalized diet, where the food is included in the personalized diet based at least in part on determining that the food satisfies at least some of the criteria.

Aspect 16: The apparatus of aspect 15 where determining that the food satisfies at least some of the criteria, further includes operations, features, circuitry, logic, means, or instructions, or any combination thereof for determining that the food satisfies criteria of a first category but not criteria of a second category and including the food in the personalized diet based at least in part on the first category having a higher priority than the second category.

Aspect 17: The apparatus of any of aspects 9 through 16, further including operations, features, circuitry, logic, means, or instructions, or any combination thereof for receiving ingredient information for a set of grocery items, where the grocery items are selected based at least in part on the ingredient information. The ingredient information may be received from an application of the one or more application, from a memory included in the electronic device, from the user, from a remote server, or from any combination thereof.

Aspect 18: The apparatus of aspect 17, further including operations, features, circuitry, logic, means, or instructions, or any combination thereof for determining, based at least in part on the received ingredient information, that a grocery item of the set of grocery items satisfies at least some of the criteria for the personalized diet, where the grocery item is included in the list of the grocery items based at least in part on determining that the grocery item satisfies at least some of the criteria.

Aspect 19: The apparatus of aspect 18 where determining that the grocery item satisfies at least some of the criteria, further includes operations, features, circuitry, logic, means, or instructions, or any combination thereof for determining that the grocery item satisfies criteria of a first category but not criteria of a second category and including the grocery item in the list of the grocery items based at least in part on the first category having a higher priority than the second category.

Aspect 20: The apparatus of any of aspects 17 through 19 where the user data includes allergy information for the user and the method, apparatuses, and non-transitory computer-readable medium, further includes operations, features, circuitry, logic, means, or instructions, or any combination thereof for determining, based at least in part on the ingredient information and the allergy information, that the user is allergic to an ingredient in a grocery item of the set of grocery items; and where selecting the grocery items includes and excluding the grocery item from the grocery items based at least in part determining that the user is allergic to the ingredient in the grocery item.

Aspect 21: The apparatus of any of aspects 9 through 20 where the user data includes medication information that indicates a medication for the user and the method, apparatuses, and non-transitory computer-readable medium, further includes operations, features, circuitry, logic, means, or instructions, or any combination thereof for receiving, from an application of the one or more applications, an indication of an interaction between a food and the medication; and where determining the personalized diet includes and excluding the food from the personalized diet based at least in part on the interaction.

Aspect 22: The apparatus of any of aspects 9 through 21, further including operations, features, circuitry, logic, means, or instructions, or any combination thereof for the user data includes medication information, allergy information, food sensitivity information, diet information, health information, fitness information, budget information, or any combination thereof and the different categories of the criteria include medication-based criteria, allergy-based criteria, food sensitivity-based criteria, diet-based criteria, health-based criteria, fitness-based criteria, budget-based criteria, or any combination thereof.

It should be noted that the methods described herein describe possible implementations, and that the operations and the steps may be rearranged or otherwise modified and that other implementations are possible. Further, portions from two or more of the methods may be combined.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof. Some drawings may illustrate signals as a single signal; however, the signal may represent a bus of signals, where the bus may have a variety of bit widths.

The terms "electronic communication," "conductive contact," "connected," and "coupled" may refer to a relationship between components that supports the flow of signals between the components. Components are considered in electronic communication with (or in conductive contact with or connected with or coupled with) one another if there is any conductive path between the components that can, at any time, support the flow of signals between the components. At any given time, the conductive path between components that are in electronic communication with each other (or in conductive contact with or connected with or coupled with) may be an open circuit or a closed circuit based on the operation of the device that includes the connected components. The conductive path between connected components may be a direct conductive path between the components or the conductive path between connected components may be an indirect conductive path that may include intermediate components, such as switches, transistors, or other components. In some examples, the flow of signals between the connected components may be interrupted for a time, for example, using one or more intermediate components such as switches or transistors.

The term "coupling" refers to condition of moving from an open-circuit relationship between components in which signals are not presently capable of being communicated between the components over a conductive path to a closed-circuit relationship between components in which signals are capable of being communicated between components over the conductive path. When a component, such as a controller, couples other components together, the component initiates a change that allows signals to flow between the other components over a conductive path that previously did not permit signals to flow.

The devices discussed herein, including a memory array, may be formed on a semiconductor substrate, such as silicon, germanium, silicon-germanium alloy, gallium arsenide, gallium nitride, etc. In some examples, the substrate is a semiconductor wafer. In other examples, the substrate may be a silicon-on-insulator (SOI) substrate, such as silicon-on-glass (SOG) or silicon-on-sapphire (SOP), or epitaxial layers of semiconductor materials on another substrate. The conductivity of the substrate, or sub-regions of the substrate, may be controlled through doping using various chemical species including, but not limited to, phosphorous, boron, or arsenic. Doping may be performed during the initial formation or growth of the substrate, by ion-implantation, or by any other doping means.

A switching component or a transistor discussed herein may represent a field-effect transistor (FET) and comprise a three terminal device including a source, drain, and gate. The terminals may be connected to other electronic elements through conductive materials, e.g., metals. The source and drain may be conductive and may comprise a heavily-doped, e.g., degenerate, semiconductor region. The source and drain may be separated by a lightly-doped semiconductor region or channel. If the channel is n-type (i.e., majority carriers are electrons), then the FET may be referred to as a n-type FET. If the channel is p-type (i.e., majority carriers are holes), then the FET may be referred to as a p-type FET. The channel may be capped by an insulating gate oxide. The channel conductivity may be controlled by applying a voltage to the gate. For example, applying a positive voltage or negative voltage to an n-type FET or a p-type FET, respectively, may result in the channel becoming conductive. A transistor may be "on" or "activated" when a voltage greater than or equal to the transistor's threshold voltage is applied to the transistor gate. The transistor may be "off" or "deactivated" when a voltage less than the transistor's threshold voltage is applied to the transistor gate.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details to providing an understanding of the described techniques. These techniques, however, may be practiced without these specific details. In some instances, well-known structures and devices are shown in block diagram form to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described herein can be implemented using software executed by a processor, hardware, firmware, hardwiring, or combinations of any of these. Features implementing functions may also be physically located at various positions, including being distributed such that portions of functions are implemented at different physical locations.

For example, the various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

As used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable read-only memory (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, digital subscriber line (DSL), or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method at an electronic device, comprising:
receiving, by an application of the electronic device, user data for a user from one or more applications of the electronic device;
determining, by a first artificial intelligence engine of the application, first criteria for the first artificial intelligence engine to use as a basis for a first personalized output for the user based at least in part on the user data;
dividing, by the first artificial intelligence engine, the first criteria into a first set of categories associated with the first personalized output;
determining, by the first artificial intelligence engine based at least in part on the user data from the one or more applications, an initial value for a weighting factor for a first category of the first set of categories;
receiving, from the user, an indication of a first priority level for the first category of the first set of categories;
modifying, by the first artificial intelligence engine, the weighting factor for the first category of the first set of categories from the initial value based at least in part on the indication of the first priority level;
determining, by the first artificial intelligence engine of the application, the first personalized output for the user based at least in part on feedback from the user and by applying weighting factors to the first set of categories, wherein the weighting factors are associated with priority levels for different categories of the first set of categories, and wherein applying the weighting factors comprises applying the weighting factor to the first category of the first set of categories;
providing, by the first artificial intelligence engine, the first personalized output to a second artificial intelligence engine of the application;
determining, by the second artificial intelligence engine of the application, second criteria for the second artificial intelligence engine to use as a basis for a second personalized output for the user based at least in part on the user data;
dividing, by the second artificial intelligence engine, the second criteria into a second set of categories associated with the second personalized output;
selecting, by the second artificial intelligence engine of the application, items for the user that are in accordance with the first personalized output and that are based at least in part on the second criteria for the second personalized output and priority levels for the second set of categories; and
outputting, by the second artificial intelligence engine, the second personalized output based at least in part on selecting the items.

2. The method of claim 1, wherein outputting the second personalized output comprises:
displaying a list of the items or communicating the list of the items to a second application.

3. The method of claim 1, further comprising:
receiving, from the user, an indication of a second priority level for a second category of the first set of categories.

4. The method of claim 3, further comprising:
determining a second weighting factor for the second category of the first criteria based at least in part on the second priority level for the second category, wherein applying the weighting factors comprises applying the second weighting factor to the second category.

5. The method of claim 3, wherein the first priority level is higher than the second priority level, and wherein the method further comprises:
determining that an item for the user satisfies criteria for the first category but not criteria for the second category; and wherein the selecting comprises:
selecting the item for the user based at least in part on the first priority level for the first category being higher than the second priority level for the second category.

6. The method of claim 1, further comprising:
communicating, by the application, a request for the user data to the one or more applications, wherein the user data is received based at least in part on communicating the request.

7. The method of claim 6, further comprising:
receiving, from the user, an indication that the application is permitted to access the one or more applications, wherein the request is communicated to the one or more applications based at least in part on receiving the indication.

8. The method of claim 1, wherein the first personalized output comprises a personalized diet and the items for the user comprise grocery items.

9. A method at an electronic device, comprising:
receiving, by an application of the electronic device, user data associated with a user from one or more applications of the electronic device;
determining, by a first artificial intelligence engine of the application, first criteria for the first artificial intelligence engine to use as a basis for a personalized diet for the user based at least in part on the user data;

dividing, by the first artificial intelligence engine, the first criteria into a first set of categories associated with the personalized diet;

determining, by the first artificial intelligence engine based at least in part on the user data from the one or more applications, an initial value for a weighting factor for a first category of the first set of categories;

receiving, from the user, an indication of a first priority level for the first category of the first set of categories;

modifying, by the first artificial intelligence engine, the weighting factor for the first category of the first set of categories from the initial value based at least in part on the indication of the first priority level;

determining, by the first artificial intelligence engine of the application, the personalized diet for the user based at least in part on feedback from the user and by applying weighting factors to the first set of categories, wherein the weighting factors are associated with priority levels for different categories of the first set of categories, and wherein applying the weighting factors comprises applying the weighting factor to the first category of the first set of categories;

providing, by the first artificial intelligence engine, the personalized diet to a second artificial intelligence engine of the application;

determining, by the second artificial intelligence engine of the application, second criteria for the second artificial intelligence engine to use as a basis for a list of grocery items for the user based at least in part on the user data;

dividing, by the second artificial intelligence engine, the second criteria into a second set of categories associated with the list of grocery items;

selecting, by the second artificial intelligence engine of the application, grocery items for the user that are in accordance with the personalized diet and that are based at least in part on the second criteria for the personalized diet and priority levels for the second set of categories; and outputting the list of grocery items based at least in part on selecting the grocery items.

10. The method of claim 9, wherein outputting the list of grocery items comprises:

displaying the list of grocery items or communicating the list of grocery items to a grocery shopping application.

11. The method of claim 10, wherein the one or more applications comprises the grocery shopping application, and wherein receiving comprises:

receiving, from the grocery shopping application, a second list of grocery items previously bought by the user, wherein the grocery items are selected based at least in part on the second list of grocery items.

12. The method of claim 9, further comprising:

receiving, from the user, an indication of the priority levels for the different categories of the first set of categories.

13. The method of claim 9, further comprising:

determining a budget for the user based at least in part on the user data, data input by the user, or both, wherein the grocery items are selected based at least in part on the budget.

14. The method of claim 9, further comprising:

receiving nutrition information for a set of foods, wherein the personalized diet is based at least in part on the nutrition information.

15. The method of claim 14, wherein the nutrition information is received from an application of the one or more applications, from a memory included in the electronic device, from the user, from a remote server, or from any combination thereof.

16. The method of claim 14, further comprising:

determining, based at least in part on the received nutrition information, that a food of the set of foods satisfies at least some of the first criteria for the personalized diet, wherein the food is included in the personalized diet based at least in part on determining that the food satisfies at least some of the first criteria.

17. The method of claim 16, wherein determining that the food satisfies at least some of the first criteria comprises:

determining that the food satisfies criteria for the first category but not criteria for a second category of the first set of categories; and including the food in the personalized diet based at least in part on the first category having a higher priority than the second category.

18. The method of claim 9, further comprising:

receiving ingredient information for a set of grocery items, wherein the grocery items are selected based at least in part on the ingredient information.

19. The method of claim 18, wherein the ingredient information is received from an application of the one or more applications, from a memory included in the electronic device, from the user, from a remote server, or from any combination thereof.

20. The method of claim 18, further comprising:

determining, based at least in part on the received ingredient information, that a grocery item of the set of grocery items satisfies at least some of the first criteria for the personalized diet, wherein the grocery item is included in the list of grocery items based at least in part on determining that the grocery item satisfies at least some of the first criteria.

21. The method of claim 20, wherein determining that the grocery item satisfies at least some of the first criteria comprises:

determining that the grocery item satisfies criteria for the first category of the first set of categories but not criteria for a second category of of the first set of categories; and including the grocery item in the list of grocery items based at least in part on the first category having a higher priority than the second category.

22. The method of claim 18, wherein the user data comprises allergy information for the user, the method further comprising:

determining, based at least in part on the ingredient information and the allergy information, that the user is allergic to an ingredient in a grocery item of the set of grocery items; and wherein selecting the grocery items comprises:

excluding the grocery item from the grocery items based at least in part determining that the user is allergic to the ingredient in the grocery item.

23. The method of claim 9, wherein the user data comprises medication information that indicates a medication for the user, the method further comprising:

receiving, from the one or more applications, an indication of an interaction between a food and the medication; and wherein determining the personalized diet comprises:

excluding the food from the personalized diet based at least in part on the interaction.

24. The method of claim 9, wherein the user data comprises medication information, allergy information, food sensitivity information, diet information, health information, fitness information, budget information, or any combination thereof, and wherein the first criteria for the first set of categories comprise medication-based criteria, allergy-based criteria, food sensitivity-based criteria, diet-based criteria, health-based criteria, fitness-based criteria, budget-based criteria, or any combination thereof.

25. An electronic device, comprising:

a processor;

memory coupled with the processor; and instructions stored in the memory and executable by the processor to cause the electronic device to:

receive, by an application of the electronic device, user data for a user from one or more applications of the electronic device;

determine, by a first artificial intelligence engine of the application, first criteria for the first artificial intelligence engine to use as a basis for a first personalized output for the user based at least in part on the user data;

divide, by the first artificial intelligence engine, the first criteria into a first set of categories associated with the first personalized output;

determine, by the first artificial intelligence engine based at least in part on the user data from the one or more applications, an initial value for a weighting factor for a first category of the first set of categories;

receive, from the user, an indication of a first priority level for the first category of the first set of categories;

modify, by the first artificial intelligence engine, the weighting factor for the first category of the first set of categories from the initial value based at least in part on the indication of the first priority level;

determine, by the first artificial intelligence engine of the application, the first personalized output for the user based at least in part on feedback from the user and by applying weighting factors to the first set of categories, wherein the weighting factors are associated with priority levels for different categories of the first set of categories, and wherein applying the weighting factors comprises applying the weighting factor to the first category of the first set of categories;

provide, by the first artificial intelligence engine, the first personalized output to a second artificial intelligence engine of the application;

determine, by the second artificial intelligence engine of the application, second criteria for the second artificial intelligence engine to use as a basis for a second personalized output for the user based at least in part on the user data;

divide, by the second artificial intelligence engine, the second criteria into a second set of categories associated with the second personalized output;

select, by the second artificial intelligence engine of the application, items for the user that are in accordance with the first personalized output and that are based at least in part on the second criteria for the second personalized output and priority levels for the second set of categories; and output the items the second personalized output based at least in part on selecting the items.

* * * * *